(12) United States Patent
Westman

(10) Patent No.: US 6,596,130 B2
(45) Date of Patent: Jul. 22, 2003

(54) PREPARATION AND USE OF IONIC LIQUIDS IN MICROWAVE-ASSISTED CHEMICAL TRANSFORMATIONS

(75) Inventor: Jacob Westman, Vänge (SE)

(73) Assignee: Personal Chemistry i Uppsala AB, Uppsala (SE)

( * ) Notice: Subject to any disclaimer, the term of this patent is extended or adjusted under 35 U.S.C. 154(b) by 0 days.

(21) Appl. No.: 09/991,730

(22) Filed: Nov. 26, 2001

(65) Prior Publication Data

US 2002/0056633 A1 May 16, 2002

Related U.S. Application Data

(63) Continuation-in-part of application No. PCT/IB00/00719, filed on May 26, 2000.

(30) Foreign Application Priority Data

May 26, 1999 (DK) ............................. 1999 00734

(51) Int. Cl.[7] .................................................. C07F 5/00
(52) U.S. Cl. ................................................. 204/157.6
(58) Field of Search ......................... 204/157.6, 157.15

(56) References Cited

U.S. PATENT DOCUMENTS

| | | | |
|---|---|---|---|
| 5,731,101 A | 3/1998 | Sherif et al. | 429/102 |
| 5,827,602 A | 10/1998 | Koch et al. | 429/194 |
| 5,883,349 A | 3/1999 | Kingston | 204/157.15 |

FOREIGN PATENT DOCUMENTS

| | | |
|---|---|---|
| AU | 1997/38559 B2 | 2/1998 |
| FR | 2 663 933 | 3/1992 |
| FR | 2 751 961 | 6/1998 |
| WO | WO 95/21871 | 8/1995 |
| WO | WO 95/21872 | 8/1995 |
| WO | WO 98/05609 A1 * | 2/1998 |
| WO | WO 98/07679 | 2/1998 |
| WO | WO 99/19288 | 4/1999 |

OTHER PUBLICATIONS

Earle, M.J. et al., Chem. Commun., 1998, pp. 2245–2246 month unavailable.
Seddon, K.R., Kinetics and Catalysis, vol. 37, No. 5, pp. 693–697 (1996) month unavailable.
Gordon, Charles M. et al., J. Mater.Chem., 1998, vol. 8, pp. 2627–2636 month unavailable.
Adams, Christopher J. et al., Chem. Commun. 1998, pp. 2097–2098 month unavailable.
Chauvin, Yves et al., Agrew. Chem. Int. Ed. Engl., 1995, vol. 34, No. 23/24, pp. 2698–2700 month unavailable.
McCormac, Paul B. et al., Synthetic Organic Chemistry in Neutral Ionic Liquids, Apr. 23, 1999.
Howarth, Joshua et al., Tetrahedron Letters, 1997, vol. 38, No. 17, pp. 3097–3100 month unavailable.
Huddleston, Jonathan G. et al., Chem. Commun., 1998, pp. 1765–1766 month unavailable.
Cablewski, Teresa et al., Journal of Organic Chemistry, vol. 59, 1994, pp. 3408–3412 month unavailable.
Raner, Kevin D. et al., Journal of Organic Chemistry, vol. 60, No. 8, pp. 2456–2460 (Apr. 21, 1995).
Seddon, Kenneth R., J. Chem. Tech. Biotechnol., vol. 68, No. 4, pp. 351–356 (Apr. 1, 1997).

* cited by examiner

Primary Examiner—Edna Wong
(74) Attorney, Agent, or Firm—Birch, Stewart, Kolasch & Birch, LLP

(57) ABSTRACT

Ionic liquids were rapidly and efficiently prepared by microwave-assisted chemical transformations. A method for performing microwave-assisted reactions, including alkylation reactions, using ionic liquids as solvent resulted in high yields with dramatically reduced reaction times. Ionic liquids, when used as an additive or co-solvent, allowed for heating, by microwave-assistance, of chemical reactions performed in traditional organic solvents, most notably non-polar solvents.

20 Claims, 1 Drawing Sheet

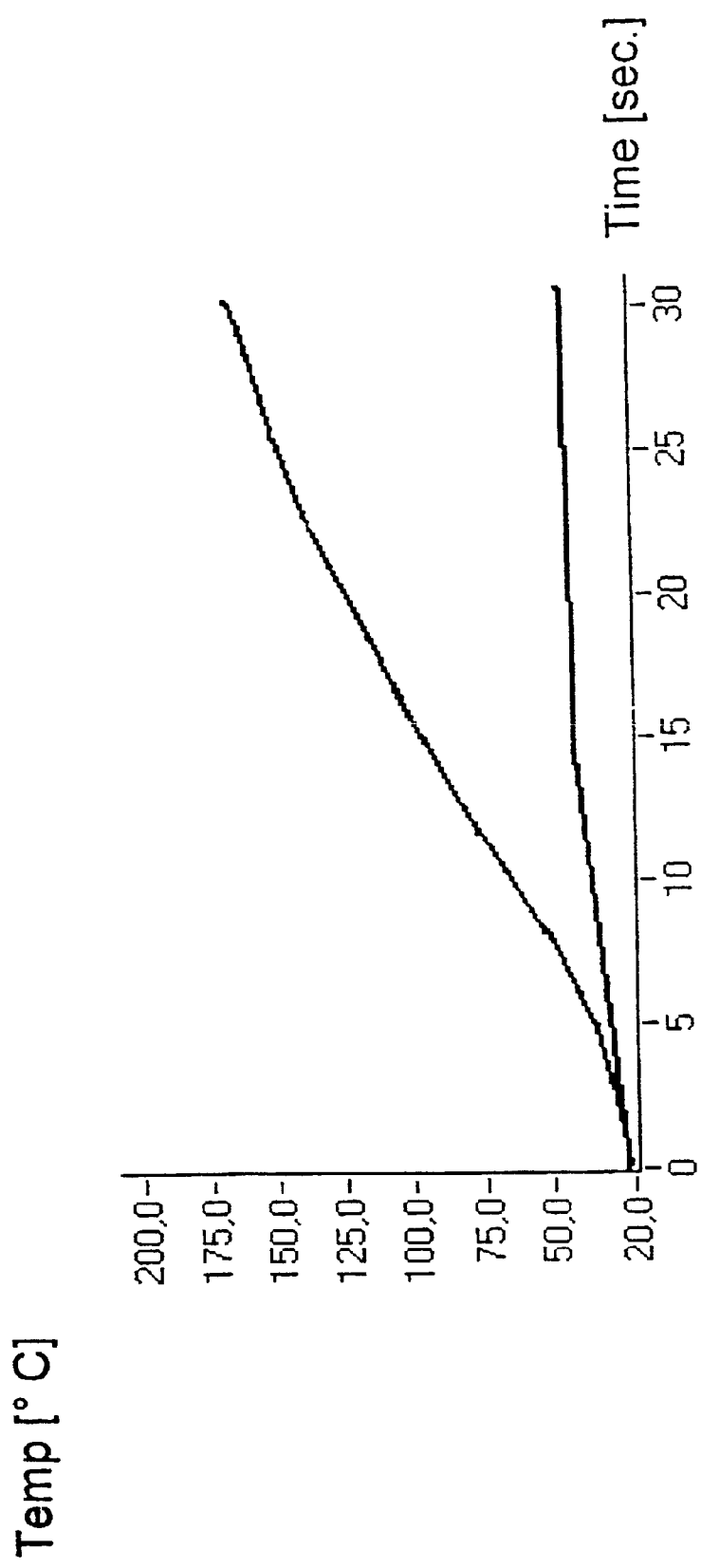

PREPARATION AND USE OF IONIC LIQUIDS IN MICROWAVE-ASSISTED CHEMICAL TRANSFORMATIONS

This application is a Continuation-In-Part of copending PCT International Application No. PCT/IB00/00719 filed on May 26, 2000, which was published in English and which designated the United States and on which priority is claimed under 35 U.S.C. § 120, the entire contents of which are hereby incorporated by reference.

FIELD OF THE INVENTION

This invention relates to the preparation and use of ionic liquids as a superb microwave energy absorbable solvent in microwave-assisted chemical transformations, in particular organic synthesis. The advantages of using low temperature ionic liquids as solvents in microwave-assisted organic synthesis are described.

BACKGROUND OF THE INVENTION

In the pharmaceutical industry, the need for an increased number of compounds for high-throughput screening puts pressure on the chemist to decrease the time for compound preparation. Microwave-assisted organic synthesis may offer an interesting solution. Microwave-assisted synthesis in organic solvents may, however, involve the risk of an explosion caused by rapid increase in the pressure of the solvent due to difficulties in controlling the application of energy to a reaction mixture.

It has then been suggested to utilise solvent-free microwave-assisted organic synthesis, in that the use of solvent-free reactions is claimed to be an environmentally friendly way of synthesis. Solvent-free synthesis is also considered a safe way of performing organic syntheses at least with respect to increased pressure from the solvent.

However, the environmentally important aspect of solvent-free synthesis is not completely fulfilled since the reagent often has to be dissolved in an organic solvent, e.g. mixed with a solid support material, before evaporation of the solvent before treatment in the microwave cavity. Consequently, organic solvents are, in reality, still used during the synthesis.

Thus, there is a need for improved techniques within in the field of microwave-assisted synthesis.

Ionic liquids are known in organic synthesis (*Chem. Commun.* (1998) 1765, *J. Am. Chem. Soc.* 98 (1976) 5277, and references 1–16 listed infra) but their use has been limited predominantly due to their limited solubility or to room temperature reactions. Thus, there is a need to expand the utility of ionic liquids in organic synthesis.

The preparation of ionic liquids is described in WO 95/21871, WO 96/18459 and U.S. Pat. No. 4,624,755. However, these methods require reactions times of up to a week, are problematic due to solubility issues, or require several hours in electrochemical cells. Thus, there is a need for improved methods within in the field of the preparation of ionic liquids.

SUMMARY OF THE INVENTION

The invention relates to a method for performing a microwave-assisted chemical transformation, wherein a ionic liquid is used as solvent. More specifically, the method entails an ionic liquid of the general formula I The invention relates to a method for performing a microwave-assisted chemical transformation, wherein an ionic liquid is used as solvent. More specifically, the method entails an ionic liquid of the general formula I

$$A^+B^- \qquad (I)$$

wherein $A^+$ is an organic cation and $B^-$ is anion, such as an inorganic anion, which in neat form at a pressure of 1 atmosphere (101.325 kPa) has a melting point of at the most 100° C.

$$A^+B^- \qquad (I)$$

wherein $A^+$ is an organic cation and $B^-$ is anion, such as an inorganic anion, which in neat form at a pressure of 1 atmosphere (101.325 kPa) has a melting point of at the most 100° C.

An object of the invention is to provide a method for performing a microwave-assisted chemical transformation, wherein an ionic liquid is used as solvent and said ionic liquid is prepared by a microwave-assisted transformation.

Furthermore, the invention relates to a method of preparing ionic liquid by a microwave-assisted transformation.

A further object of the invention is to provide a method of performing a microwave-assisted preparation of an ionic liquid followed by performing a microwave-assisted chemical transformation in one pot wherein said ionic liquid is used as solvent, such as sole solvent, predominant solvent, co-solvent, or additive to an organic solvent in said microwave-assisted chemical transformation.

BRIEF DESCRIPTION OF THE DRAWINGS

FIG. 1 demonstrates the impact of the addition of ionic liquids on the temperature increase of dioxane at 300 W microwave irradiation by comparing the two depicted curves. The lower curve represents dioxane heated over time with microwave energy and the upper curve represents dioxane with the addition of 2 vol % butyl-methyl-imidazolium hexafluorophosphate.

DESCRIPTION OF THE INVENTION

The present inventor has now found that the excellent dielectric properties of ionic liquids offer hitherto unrealised advantages in a method when low-temperature ionic liquids are used as solvents for microwave-assisted chemical transformation.

The present invention provides a method for performing a microwave-assisted chemical transformation, wherein a low-temperature ionic liquid is used as a solvent. The term "solvent" is intended to mean acting as sole solvent, predominant solvent, co-solvent, or additive to an organic solvent used in performing a microwave-assisted chemical transformation.

The term "microwave" is intended to have is generally accepted meaning, namely covering electromagnetic radiation of a frequency in the range of 300 MHz to 300 GHz. However, preferably, microwave radiation of a frequency in the range of 500 MHz to 100 GHz is used to assist the chemical transformation.

By the term "ionic liquid" is meant liquids that are comprised entirely of ions. Thus, molten sodium chloride is in principle an ionic liquid at a fairly high temperature (above 1074° C.). The present invention, however, relates to a method where low temperature ionic liquids are used.

The term "low temperature" when used in relation to ionic liquids is intended to mean an ionic liquid which in neat form at a pressure of 1 atmosphere (101.325 kPa) has a melting point of at the most 100° C., preferably at the most 60° C., in particular at the most 30° C., especially at the most 15° C.

As mentioned above, the present invention i.a. relates to a method for performing a microwave-assisted chemical transformation using an ionic liquid as solvent. Generally, the term "chemical transformation" should be interpreted in the broadest sense. Examples of "chemical transformations" range from (a) the formation of new chemical entities (covalent bond formation) via the reaction of a chemical species with one or more reagents optionally under the influence of a catalyst, (b) racemisation of chemical species, and (c) isomerisation/rearrangement of chemical species, to (d) formation of affinity pairs. Especially interesting chemical reactions are organic reactions, i.e. chemical reactions involving an organic compound. Typical organic reactions types are polymerisation/oligomerisation, esterification, decarboxylation, hydrogenation, dehydrogenation, addition such as 1,3-dipolar addition, oxidation, isomerisation, acylation, alkylation, amidation, arylation, Diels-Alder reactions such as maleinisation and fumarisation, epoxidation, formylation, hydrocarboxylation, hydroboration, halogenation, hydroxylation, hydrometallation, reduction, sulphonation, aminomethylation, ozonolysis, heterocyclisation etc.

The ionic liquid is preferably a compound of the general formula I $$A^+B^-\qquad\qquad(I)$$

wherein $A^+$ is a cation and $B^-$ is anion, preferably wherein $A^+$ is an organic cation and $B^-$ is an inorganic or organic anion, said ionic liquid in its neat form at a pressure of 1 atmosphere (101.325 kPa) having a melting point of at the most 100° C., preferably at the most 60° C., in particular at the most 30° C., especially at the most 15° C.

The term "organic cation" is intended to mean an organic molecule wherein a non-metal atom has donated one or more electrons to another atom or atoms so that the organic molecule has become a positively charged species: a cation. The positive charge could be either concentrated to one atom or distributed over the whole molecule. As an example, the charged on 1-butyl-3-methyl imidazolium cation is delocalized over the entire ring system.

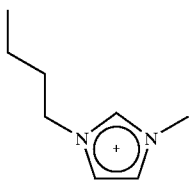

An interesting organic cation is an N-substituted cation where the cationic functionality is essentially associated with the nitrogen atom. A particularly interesting organic cation is of the type where the N-substituted cation is an N-substituted N-heteroaromatic cation wherein the cationic functionality is associated with the nitrogen atom-containing heteroaromatic structure.

In particular, the cation has the general formula $[RX]^+$ where X is a nitrogen containing entity and R is $C_{1-20}$-alkyl (typically $C_{1-6}$-alkyl) which is bound to the nitrogen atom of the nitrogen containing entity. Examples of such cations are pyridinium, pyridazinium, pyrimidinium, pyrazinium, imidazolium, pyrazolium, thiazolium, oxazolium, isoxazolium, triazolium, where the nitrogen in the aromatic ring is substituted with $C_{1-20}$-alkyl. Here, as generally, "$C_{1-20}$-alkyl" is intended to mean a linear, cyclic or branched hydrocarbon group having 1 to 20 carbon atoms, such as methyl, ethyl, propyl, iso-propyl, cyclopropyl, butyl, tert-butyl, iso-butyl, cyclobutyl, pentyl, cyclopentyl, hexyl, cyclohexyl, hexadecyl, heptadecyl, octadecyl, nonadecyl. Analogously, the term "$C_{1-6}$-alkyl" is intended to mean a linear, cyclic or branched hydrocarbon group having 1 to 6 carbon atoms, such as methyl, ethyl, propyl, iso-propyl, pentyl, cyclopentyl, hexyl, cyclohexyl.

Particularly interesting cations are selected from 1-($C_{1-20}$-alkyl)-3-($C_{1-20}$-alkyl)-imidazolium cation and 1-($C_{1-20}$-alkyl)-pyridinium cations, typically 1-($C_{1-6}$-alkyl)-3-($C_{1-6}$-alkyl)-imidazolium cation and 1-($C_{1-6}$-alkyl)-pyridinium cations.

With respect to the anion, it may be an organic or inorganic anion. A number of possibilities known to the person skilled in the art are available. Illustrative examples of inorganic anions are those selected from $F^-$, $Cl^-$, $Br^-$, $I^-$, $NO_3^-$, $BF_4^-$, $PF_6^-$, $FeCl_4^-$, $ZnCl_3^-$, $SnCl_5^-$, $AsF_6^-$, $SbF_6^-$, $AlCl_4^-$, $CF_3COO^-$, $NiCl_3^-$, $(CF_2SO_3^-)_2$, $(CF_3)_2PF_4^-$. Illustrative examples of organic anions or carboxylic anion include lactate or tartrate, preferably in their chiral forms.

It should be understood that in one embodiment of the invention, the anion may participate in the chemical transformation, e.g. as a catalyst and/or a Lewis acid, e.g. in Friedel-Crafts reactions. As an example, $AlCl_4^-$ can, in accordance with the present invention, act as a Lewis acid catalyst (depending on the proportion of $AlCl_3$ added to the melts) in Friedel-Crafts microwave-assisted reactions performed in an ionic liquid. In a preferred embodiment, the anion of the ionic liquid is involved in the chemical transformation as a reactant or catalyst.

In an alternative embodiment of the invention however, the anion is chemically inert. That is to say that the anion does not participate in nor interfere with the reaction. This embodiment is anticipated when the anion is neutral, i.e. neither acidic nor basic, thus not participating in nor interfering with the reaction.

With respect to the specific ionic liquids, it is believed that numerous suitable combinations of the above-mentioned organic cations and the inorganic anions exist. At present, however, it is believed that room-temperature ionic liquids selected from chloroaluminiate ionic liquids such as 1-n-butylpyridinium chloride-aluminium (III) chloride and 1-ethyl-3-methylimidazolium chloride-aluminium (III) chloride, $C_{1-20}$-dialkyl-imidazolium hexafluorophosphates such as 1-butyl-3-methyl-imidazolium hexafluorophosphate, N-$C_{1-20}$-alkyl-pyridinium hexafluorophosphates such as 3- and 4-methyl-N-$C_{1-20}$-alkyl pyridinium hexafluorophosphate such as 1-butyl-3-methyl-imidazolium tetrafluoroborate are particularly advantageous.

The ionic liquids useful within the present invention are typically fluid at room temperature and have a liquid range up to 300° C. and more at standard pressure (water only has 100° C.). They should be stable up to at least 200° C. Unlike water and other hydrophilic solvents, they will dissolve a wide range of organic molecules to an appreciable extent (benzene form 50% (v/v) solution in 1-butyl-3-methyl-imidazolium hexafluorophosphate). They have the possibility for in situ generation of anions which makes them suitable solvents for almost all reactions involving charged intermediates along their reaction pathways such as acylation and alkylation. It is also shown in the literature that ionic liquids are a very useful solvent for palladium assisted organic reaction since the catalyst seems to be very stable in ionic liquids compared with organic solvents or water.

Ionic liquids are comprised entirely of ions and therefore absorb microwave irradiation in a very efficient way. Given they do not exhibit any significant vapour pressure (at least up to 500° C.), they are suitable for microwave heating. Moreover, with microwave assistance, ionic salts are miscible with non-polar solvents. Thus, ionic liquids make it possible to use non-polar solvents, which do not themselves absorb microwaves and then do not get hot by microwave energy. With the use of an ionic liquid as an additive, a solvent such as dioxane may get heated very rapidly from microwave energy. Thus, in one embodiment of the invention, a microwave-assisted chemical transformation is performed wherein an ionic liquid is used as an additive to an organic solvent for said chemical transformation. As illustrated in FIG. 1, small amounts of ionic liquids suffice to heat nonpolar organic solvents, such as at least 0.1 vol %, such as at least 0.25 vol %, preferably at least 1, 2, 3, 4, or 5 vol %. Thus, ionic liquids, when used as an additive or co-solvent to traditional organic solvents, allow for heating, by microwave-assistance, of chemical reactions performed in traditional organic solvents, notably non-polar solvents. Consequently, one embodiment of the invention is a method of performing a microwave-assisted chemical transformation, wherein a traditional solvent, such as a polar organic solvent, a non-polar solvent or water, is used in said chemical transformation and wherein ionic liquids are used as an additive or co-solvent.

The impact of the addition of ionic liquids on the temperature increase of dioxane at 300 W microwave irradiation is demonstrated by comparing the two curves of FIG. 1. The lower curve represents dioxane heated over time with microwave energy and the upper curve represents dioxane with the addition of 2 vol % butyl-methyl-imidazolium hexafluorophosphate.

Thus, microwave-assisted chemical transformations in conventional organic solvents using ionic liquids as additives may proceed at a much faster rate It is anticipated by the present invention that more than one ionic liquid may simultaneously be used as an additive to an organic solvent used in a chemical transformation.

The use of ionic liquids as additives in an organic solvent system in microwave-assisted chemical transformation may be limited by the vapour pressure of the traditional solvent. Thus, in an attractive embodiment of the invention, an ionic liquid may be used as the predominant or sole solvent in a microwave-assisted chemical transformation.

In a preferred embodiment, the ionic liquid is substantially the only solvent for the chemical transformation. However, as will be appreciated by the person skilled in the art, certain liquid reagents may have the capacity to dissolve or contribute to the dissolution of other reaction components. Furthermore, certain bases and acids may be capable of performing a dual role in the reaction. That is to say they may act as bases or acids and serve to contribute to the dissolution of other reaction components. Still further, certain bases or acids are sold commercially as solutions. It is thus anticipated that when one combines the possible contributory assistance to dissolution by the liquid reagents (e.g. liquid bases, or, as in Examples 3 and 4, the liquid substrate benzyl alcohol or benzyl amine, respectively) and the possible contributory assistance to dissolution by the solvent present in commercially available reagents, a minor component of the liquid volume, such as less than 10 vol %, such as less than 5 vol %, 4 vol %, 3 vol %, 2 vol % or less than 1 vol % of the solvent is not ionic liquid. Thus, in these embodiments, an ionic liquid is the predominant solvent.

It is anticipated by the present invention that one or more ionic solvent may be combined to be used as sole solvent in a chemical transformation. Furthermore, in embodiments wherein an ionic liquid is used as predominant or co-solvent in a chemical transformation, one or more ionic liquids may be combined with a solvent which is not an ionic liquid, such as a traditional organic solvent. That is to say that the ionic liquid acts as co-solvent.

Advantageously, ionic liquids exhibit a very low vapour pressure, enhancing their suitability even further for microwave heating. Furthermore, a number of unexpected practical advantages when performing microwave-assisted chemical transformations wherein an ionic liquid is used as solvent. As demonstrated by exemplary data below (Example 1), the invention i.a results in reaction times almost one percent in duration when compared to the use of ionic liquids as solvent at room temperature. Equally advantageous to a dramatic reduction in reaction times under equivalent reaction conditions is the surprising result that this dramatic reduction in reaction times is also achieved when the quantity and reactivity of the reagent is reduced, thus being more cost efficient. The advantage of the use less reactive reagents and catalytic reagents results in potentially milder reaction conditions and the possibility of selecting reagents and catalyst conventionally considered inappropriate.

Ionic liquids may be chemically inert. However, as stated, in certain embodiments the anion, the cation or the ion pair may perform a catalytic function in the reaction. Furthermore, as will be appreciated by the person skilled in the art, certain physical properties of the ionic liquid, such as the dielectric constant, have a contributory influence on the reaction rate, level of the reaction potential, and other determinants of the feasibility of a reaction and reaction time and yield.

Generally, the chemical transformation may comprise of combining solid and/or liquid reagents with each other and with room-temperature ionic liquids and elevation of the temperature of the mixture by means of microwave energy. Furthermore, the chemical transformation may comprise dissolving a reactant in a room-temperature ionic liquid and elevation of the temperature of the ionic liquid mixture comprising the reactant by means of microwave radiation. It should be understood that the temperature may be elevated to above 100° C., such as above 150° C., e.g. above 200° C. at standard pressure, even without any means for controlling the pressure in the vessel wherein the chemical transformation is performed.

Ionic liquids absorb microwave radiation energy extremely well and this advantageous feature makes it feasible to rapidly reach the activation energy needed for the reaction, e.g. the transition state, within few seconds, and thereby eliminating the formation of any side-products. Short reaction times also decrease the amount of breakdown products since the sample could actively be chilled after the reaction. Thus, it is possible to quickly reach the optimal temperature and once the reaction is complete, the temperature can be quickly reduced so as to minimise side products and breakdown products. Since the reaction time is very short, it is possible to develop and optimise a given synthesis in a very short time span.

The solvent is also useful since the purification could be very efficient in that purification by liquid—liquid extraction normally can be quite tedious as some solvents used in organic chemistry are at least slightly soluble in both water and organic solvent. Some ionic liquids, e.g. 1-butyl-3-methyl-imidazolium hexafluorophosphate are immiscible with both certain organic solvents such as hexane, dialkylether as well as with water which means that it is possible to perform three-phase extractions. This procedure is believed to speed up the purification step.

An object of the present invention is to provide a method of performing a microwave-assisted preparation of an ionic liquid. Generally, the ionic liquid may be prepared by assisting with microwave energy a transformation described or cited in references listed infra or using reagents used in WO 95/21871, WO 96/18459 and U.S. Pat. No. 4,624,755. The microwave-assisted preparation of ionic liquids according the invention is advantageous over conventional methods in that the reaction times are typically much faster and there are less side-products thus resulting in higher yields, simpler purification and greater recovery.

The preparation of ionic liquids typically comprises combining organic species capable of becoming a positively charged species (a cation), such as a nitrogen atom-containing heteroaromatic compound, with a $C_{1-20}$-alkyl halide, such as an alkyl-fluoride, chloride, bromide or iodide and irradiating said mixture with microwaves for the required time, such as less than 30 min., preferably less than 15 min., most preferably for less than 10 min., 5 min., or less than 2 minutes. The organic species capable of becoming a cation, in preferred embodiments, are selected from the group comprising pyridine, pyridazine, pyrimidine, pyrazine, imidazole, pyrazole, thiazole, oxazole, isoxazole, triazole, where the nitrogen in the aromatic ring is substituted with $C_{1-20}$-alkyl. The combining of the organic species capable of becoming a cation and with a $C_{1-20}$-alkyl halide may be done in a conventional organic solvent or water as may be the irradiating of the mixture with microwave energy.

The method of preparing ionic liquid by a microwave-assisted transformation according to the invention typically comprises combining a nitrogen atom-containing heteroaromatic compound selected from 1-($C_{1-20}$-alkyl)-imidazoles, 3-($C_{1-20}$-alkyl)-imidazoles or 1-($C_{1-20}$-alkyl)-pyridines, with a $C_{1-20}$-alkyl halide, such as an alkyl-fluoride chloride, bromide or iodide, and irradiating said mixture with microwaves for the necessary time, such as less than 30 min., preferably less than 15 min., most preferably for less than 10 min., 5 min., or less than 2 minutes. Typically, the nitrogen atom-containing heteroaromatic compound is selected from 1-($C_{1-6}$-alkyl)-imidazoles, a 3-($C_{1-6}$-alkyl)-imidazoles and 1-($C_{1-6}$-alkyl)-pyridines.

The method of preparing ionic liquid by a microwave-assisted transformation according to the invention may further comprise combining the product after said irradiation with a salt of anion selected from the group consisting of $F^-$, $Cl^-$, $Br^-$, $I^-$, $NO_3^-$, $BF_4^-$, $PF_6^-$, $FeCl_4^-$, $ZnCl_3^-$, $SnCl_5^-$, $AsF_6^-$, $SbF_6^-$, $AlCl_4^-$, $CF_3COO^-$, $NiCl_3^-$, $(CF_2SO_3^-)_2$, $(CF_3)_2PF_4^-$, and carboxylic anions such as lactate and tartrate. Preferably, carboxylic anions such as lactate and tartrate are in one of their chiral forms.

A further object of the invention is to provide a method of performing a microwave-assisted preparation of an ionic liquid followed by performing a microwave-assisted chemical transformation in one pot wherein said ionic liquid is used as solvent, such as sole solvent, predominant solvent, co-solvent, or additive to an organic solvent in said microwave-assisted chemical transformation.

An object of the invention is to provide a method for performing a microwave-assisted chemical transformation, wherein an ionic liquid is used as solvent and said ionic liquid is prepared by a microwave-assisted transformation.

Some of the ionic liquid are immiscible with saturated hydrocarbon solvent, like dialkyl ethers and heptane and water which make the purification step very easy (extraction) and environmentally acceptable since ionic liquids could be reused several times.

The limitation with up scaling in microwave-assisted organic synthesis today is that the construction of microwave ovens that produce enough energy is a problem. Due to the fact that ionic liquids absorb microwave energy in a very efficient way, the energy output from the power supply is not a limitation. Therefore, ionic liquids are also believed to be very suitable solvents for large-scale microwave-assisted organic synthesis, e.g. for reaction mixtures of more than 100 L.

General References to Organic Chemistry Performed by Using Ionic Liquids

1. Regioselective alkylation in ionic liquids, J. Earle, P. B. McCormac, K. R. Seddon, *Chem. Commun.* (1998) 2245–2246.
2. Room temperature ionic liquids as novel media for "clean" liquid—liquid extraction J. G. Huddleston, H. D. Willauer, R. P. Swatloski, A. E. Visser, R. D. Rogers *Chem. Commun.* (1998) 1765–1766.
3. A novel class of versatile solvents for two-phase catalysis: hydrogenation, isomerization and hydroformylation of alkenes catalyzed by rhodium complexes in liquid 1,3-dialkylimidazolium salts, Y. Chauvin, L. Mussmann, H. Olivier. *Angew. Chem. Int. Ed. Engl.* 34 (1995) 2698–2700.
4. Friedel-Crafts reactions in room temperature ionic liquids C. J. Adams, M. J., Earle, G. Roberts., K. R. Seddon, *Chem. Commun.* (1998), 2097–2098.
5. 1-ethyl-3-methylimidazolium halogenoaluminate ionic liquids as reaction media for the acylative cleavage of ethers. L. Green, I. Hemeon, R. D. Singer, *Tetrahedron Lett.* 41 (2000)1343–1346.
6. Moisture Stable dialkylimidazolium salts as heterogeneous and homogeneous Lewis acids in the Diels-Alder reaction, J. Howarth, K., Hanlon, D. Fayne, P. McCormac, *Tetrahedron Lett.* 38 (1997) 3097–3100.
7. 1-Ethyl-3-methylimidazolium halogenoaluminate melts as reaction media for the Friedel-Crafts acylation of ferrocene, J. K. D. Surette, L. Green, R. D. Singer, *Chem. Commun.*, (1996) 2753–2754.
8. Ionic liquid crystals: hexafluorophaspate salts, C. M. Gordon, J. D:, Holbrey, A. R. Kennedy, K. R. Seddon, *J. Mater. Chem.* 8 (1998) 2627–2636.
9. Room-temperature ionic liquids: Neoteric solvents for clean catalysis, K. R. Seddon. *Kinetics and Catalysis* 37 (1996) 693–697.
10. Friedel-Crafts reactions in ambient temperature molten salts, J. A: Boon, J. A. Levisky, J. L. Pflug, J. S. Wilkes, *J. Org. Chem.* 51 (1986) 480–483.
12. Novel photochemical behaviour of anthracene in a room temperature molten salt, G. Hondrogiannis, C. W. Lee, R. M. Pagni, G. Mamantov, *J. Am. Chem. Soc.*, 115 (1993) 9828–9829.
13. Electroinitiated Friedel-Crafts transalkylations in a room-temperature molten salt medium, V. R., Koch, L. L. Miller, R. A. Osteryoung, *J. Am. Chem. Soc.* 98 (1976) 5277–5284.
14. Brönsted superacidity of HCl in a liquid chloroaluminate. $AlCl_3$-1-Ethyl-3-methyl 1H-imidazolium chloride, G. P. Smith, A. S. Dworkin, R. M. Pagni, S. P. Zingg, *J. Am. Chem. Soc.* 111, (1989) 525–530.
15. Heck reaction catalysed by phospa-palladacycles in non-aqueous ionic liquids, W. A. Hermann, V. P. W. B öhm, *J. Orgmet. Chem.*, 572, (1999) 141–145.
16. The Heck reaction in ionic liquids: A multiphasic catalyst system, A. J: Carmichael, M. J. Earle, J. D. Holbrey, P. B. McCormac, K. R. Seddon, *Org. Lett.*, 1(7), (1999) 997–1000.

As stated, ionic liquids consist entirely of ions and therefore absorb microwave irradiation in a very efficient way. Furthermore, they exhibit a very low vapour pressure, enhancing their suitability even further for microwave heating. Despite ionic liquids being salts, they dissolve to an appreciable extent in a wide range of organic solvents when assisted by microwave energy as compared to water and alcohols. Some ionic liquids are also soluble in many non-polar organic solvents and therefore have been used as microwave coupling agents, when microwave transparent solvents are employed.

EXAMPLES

Example 1

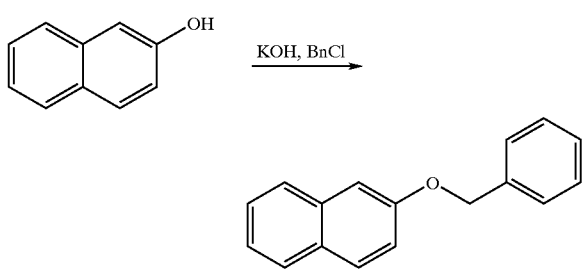

0.35 mmol 2-naphtol was dissolved in 2 ml 1-ethyl-3-methylimidazolium tetrafluoroborate. 1.5 equiv. of BnCl and 2 equiv. of KOH was added. The reaction was run in a microwave apparatus at 200° C. for 2 min. The product is extracted with diethyl ether and analysed with TLC and LC/MS. The product was formed in a quantitative yield.

In comparison, alkylation of 2-naphtol and indole has been performed in an ionic liquid by Earle et al. (M. J. Earle, P. B. McCormac, K. R. Seddon, Chem. Commun. (1998) 2245–2246). These reactions were carried out, typically as 10% w/v solutions of 2-naphtol or indole in 1-butyl-3-methylimidazolium hexafluorophosphate using 1.3 to 2 equiv. of benzyl bromide and 2 equiv. of KOH. Reactions were complete in 2–3 h at room temperature with almost quantitative extraction of products.

This comparative result shows that it is possible to reduce the reaction time even when the amount and reactivity of the reagent is reduced (and not only reaction time is reduced (benzyl chloride instead of benzyl bromide). It is also possible to use less reactive catalytic reagents such as Ba(OH)$_2$ instead of KOH. Ba(OH)$_2$ is a poorer base which mean "milder" reaction condition.

Example 2

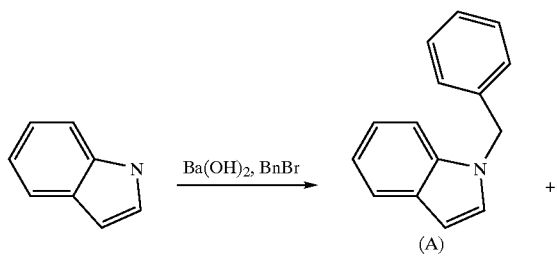

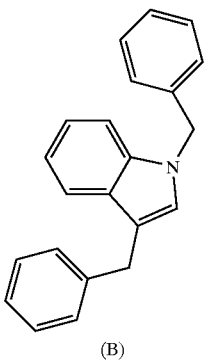

0.35 mmol indole was dissolved in 2 ml 1-butyl-3-methylimidazolium hexafluorophosphate. 1.5 equiv. of BnBr 1 and 2 equiv. of Ba(OH)$_2$ was added. The reaction was run in a microwave apparatus at 180° C. for 1 min. The product is extracted with diethyl ether and analysed with TLC and LC/MS. Result: The desired product (A) was formed in >90% yield and the debenzylated product (B) was formed in 5% yield. The reaction was also performed with K$_2$CO$_3$ as the base. Product is formed but the reaction is slightly slower. The reaction was not optimised.

Example 3

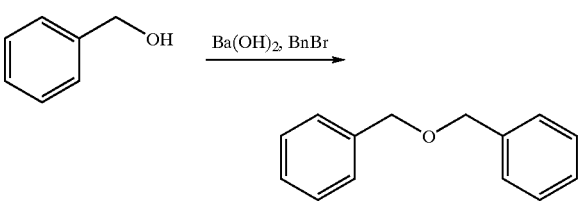

0.35 mmol benzyl alcohol was dissolved in 2 ml 1-Butyl-3-methylimidazolium hexafluorophosphate. 1.5 equiv. of BnBr and 2 equiv. of Ba(OH)$_2$ was added. The reaction was run in a microwave apparatus at 160° C. for 3 min. The product is extracted with diethyl ether and analysed with TLC and LC/MS. Results: The product was formed in >90% yield.

Example 4

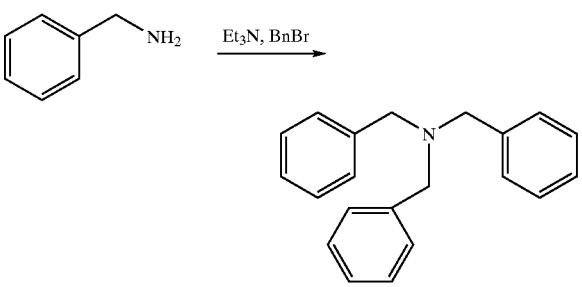

0.35 mmol benzylamine was dissolved in 2 ml 1-Butyl-3-methylimidazolium hexafluorophosphate. 1.5 equiv. of BnBr and 2.2 equiv. of Et$_3$N were added. The reaction was run in a microwave apparatus at 180° C. for 120 sec. The product is extracted with diethyl ether and analysed with TLC and LC/MS. Result: The product was formed in a quantitative yield. The same result was found when $K_2CO_3$ was used as the base.

Example 5

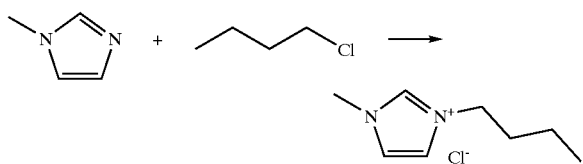

Methylimidazole and 11 mmol of 1-Chlorobutane were mixed together with 0.1 mL of Ethyl acetate and irradiated with microwaves at 170° C. for 5 min. The residue was put in the freezer where the product is precipitated. No purification was needed.

Example 6

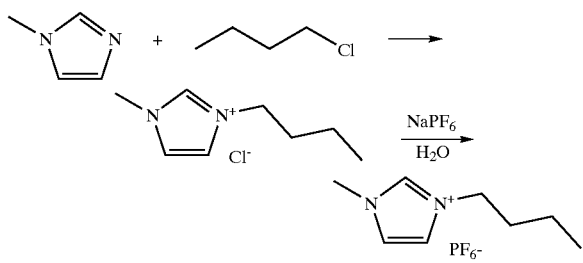

10 mmol of 1-Methylimidazole and 11 mmol of 1-Chlorobutane were mixed together with 0.1 mL of Ethyl acetate and irradiated with microwaves at 170° C. for 5 min. 11 mmol of Sodium hexafluorophosphate in 2 mL of water was added and the mixture is heated for 100° in 2 min. The residue was separated (two-phase system) and the ionic liquids is extracted with water and dried in vacuo. No further purification was needed.

What is claimed is:

1. A method for performing a microwave-assisted chemical transformation, said method comprising elevation of the temperature by means of microwave radiation of a mixture comprising an organic compound and an ionic liquid of the general formula (I), $$A^+B^- \quad (I)$$

wherein $A^+$ is an organic cation and $B^-$ is an anion, and wherein said ionic liquid in neat form at a pressure of 1 atmosphere has a melting point of at the most 100° C., as a solvent.

2. The method according to claim 1, wherein the ionic liquid has a melting point of at the most 60° C.

3. The method according to claim 1, wherein the organic cation is an N-substituted cation where the cationic functionality is associated with the nitrogen atom.

4. The method according to claim 3, wherein the N-substituted cation is an N-substituted N-heteroaromatic cation wherein the cationic functionality is associated with the nitrogen atom.

5. The method according to claim 4, wherein the cation is selected from the group consisting of pyridinium, pyridazinium, pyrimidinium, pyrazinium, imidazolium, pyrazolium, thiazolium, oxazolium, isoxazolium, and triazolium, where the nitrogen in the aromatic ring is substituted with $C_{1-20}$-alkyl.

6. The method according to claim 5, wherein the cation is selected from the group consisting of 1-$C_{1-20}$-alkyl-3-$C_{1-20}$-alkyl imidazolium cation and 1-$C_{1-20}$-alkylpyridinium cation.

7. The method according to claim 3, wherein the cation has the general formula $[RX]^+$ where X is a nitrogen containing entity and R is $C_{1-20}$-alkyl which is bound to the nitrogen atom of the nitrogen containing entity.

8. The method according to claim 1, wherein the anion is selected from the group consisting of $F^-$, $Cl^-$, $Br^-$, $I^-$, $NO_3^-$, $BF_4^-$, $PF_6^-$, $FeCl_4^-$, $ZnCl_3^-$, $SnCl_5^-$, $AsF_6^-$, $SbF_6^-$, $AlCl_4^-$, $CF_3COO^-$, $NiCl_3^-$, $(CF_2SO_3^-)_2^-$, $(CF_3)_2PF_4^-$, and a chiral or achiral tartrate or lactate.

9. The method according to claim 1, wherein the ionic liquid is selected from the group consisting of chloroaluminiate ionic liquids, $C_{1-20}$-alkyl-imidazolium hexafluorophosphate, and 1-butyl-3-methyl-imidazolium tetrafluoroborate.

10. The method according to claim 1, wherein the anion of the ionic liquid is involved in the chemical transformation as a reactant.

11. The method according to claim 1, wherein the ionic liquid is substantially the only solvent for the chemical transformation.

12. The method according to claim 1, wherein the ionic liquid is a co-solvent or an additive to an organic solvent.

13. The method according to claim 1, wherein the chemical transformation comprises dissolving a reactant in said ionic liquid and elevation of the temperature of the ionic liquid mixture comprising the reactant by said means of microwave radiation.

14. The method according to claim 1, wherein microwave radiation of a frequency in the range of 500 MHz to 100 GHz is used to assist the chemical transformation.

15. A method according to claim 1, wherein said ionic liquid is prepared by a microwave-assisted transformation.

16. A method of preparing an ionic liquid by a microwave-assisted transformation, said method comprising elevation of the temperature by means of microwave radiation of a mixture comprising an organic species capable of becoming an organic cation and a $C_{1-20}$-alkyl halide, and optionally combining the product thereof with a salt of an anion selected from the group consisting of $F^-$, $Cl^-$, $Br^-$, $I^-$, $NO_3^-$, $BF_4^-$, $PF_6^-$, $FeCl_4^-$, $ZnCl_3^-$, $SnCl_5^-$, $AsF_6^-$, $SbF_6^-$, $AlCl_4^-$, $CF_3COO^-$, $NiCl_3^-$, $(CF_2SO_3^-)_2$, $(CF_3)_2PF_4^-$, and carboxylic anions, whereby an ionic liquid of the general formula (I)

$$A^+B^- \quad (I)$$

wherein $A^+$ is an organic cation and $B^-$ is an anion, and wherein said ionic liquid in neat form at a pressure of 1 atmosphere has a melting point of at the most 100° C. is formed.

17. A method according to claim 16, wherein the organic species capable of becoming a positively charged species is a nitrogen atom-containing heteroaromatic compound.

18. A method according to claim 17, wherein the nitrogen atom-containing heteroaromatic compound is selected from the group consisting of 1-($C_{1-20}$-alkyl)-imidazoles, 3-($C_{1-20}$-alkyl)-imidazoles and 1-($C_{1-20}$-alkyl)-pyridines, and the irradiating of said mixture with microwaves is for less than 30 min.

19. A method according to claim 18, wherein the nitrogen atom-containing heteroaromatic compound is selected from 1-($C_{1-6}$-alkyl)-imidazoles, a 3-($C_{1-6}$-alkyl)-imidazoles and 1-($C_{1-6}$-alkyl)-pyridines.

20. A method for preparation of an ionic liquid and a chemical transformation in one pot which comprises performing a microwave-assisted preparation of an ionic liquid by elevation of the temperature by means of microwave radiation of a mixture comprising an organic species capable of becoming an organic cation and a $C_{1-20}$-alkyl halide, and optionally combining the product thereof with a salt of an anion selected from the group consisting of $F^-$, $Cl^-$, $Br^-$, $I^-$, $NO_3^-$, $BF_4^-$, $PF_6^-$, $FeCl_4^-$, $ZnCl_3^-$, $SnCl_5^-$, $AsF_6^-$, $SbF_6^-$, $AlCl_4^-$, $CF_3COO^-$, $NiCl_3^-$, $(CF_2SO_3^-)_2$, $(CF_3)_2PF_4^-$, and carboxylic anions, whereby an ionic liquid of the general formula (I)

$$A^+B^- \qquad (I)$$

wherein $A^+$ is an organic cation and $B^-$ is an anion, and wherein said ionic liquid in neat form at a pressure of 1 atmosphere has a melting point of at the most 100° C. is formed; followed by performing a microwave-assisted chemical transformation by elevation of the temperature by said means of microwave radiation of a mixture comprising an organic compound and said ionic liquid of the general formula (I), $$A^+B^- \qquad (I)$$

wherein $A^+$ is an organic cation and $B^-$ is an anion, and wherein said ionic liquid in neat form at a pressure of 1 atmosphere has a melting point of at the most 100° C., as a solvent, in one pot.

* * * * *